(12) United States Patent
Mainde et al.

(10) Patent No.: US 8,747,920 B2
(45) Date of Patent: Jun. 10, 2014

(54) PHARMACEUTICAL COMPOSITIONS COMPRISING NON-STEROIDAL ANTIINFLAMMATORY DRUG, ANTIPYRETIC-ANALGESIC DRUG AND PROTON PUMP INHIBITOR

(75) Inventors: Chandrashekhar Mainde, Nagpur (IN); Pradeep Ramdas Wahile, Buldhana (IN)

(73) Assignee: Wockhardt Ltd., Bandra-Kurla Complex, Bandra East, Mumbai (IN)

( * ) Notice: Subject to any disclaimer, the term of this patent is extended or adjusted under 35 U.S.C. 154(b) by 864 days.

(21) Appl. No.: 12/226,524

(22) PCT Filed: Apr. 27, 2007

(86) PCT No.: PCT/IB2007/001110
§ 371 (c)(1),
(2), (4) Date: Mar. 23, 2009

(87) PCT Pub. No.: WO2007/129178
PCT Pub. Date: Nov. 15, 2007

(65) Prior Publication Data
US 2009/0220591 A1    Sep. 3, 2009

(30) Foreign Application Priority Data

| Apr. 28, 2006 | (IN) | ............................ 665/MUM/2006 |
| Apr. 28, 2006 | (IN) | ............................ 666/MUM/2006 |
| Apr. 28, 2006 | (IN) | ............................ 667/MUM/2006 |
| Apr. 28, 2006 | (IN) | ............................ 668/MUM/2006 |

(51) Int. Cl.

| A61K 9/14 | (2006.01) |
| A01N 65/00 | (2009.01) |
| A61K 31/445 | (2006.01) |
| A61K 31/235 | (2006.01) |
| A61K 31/16 | (2006.01) |
| A61K 9/48 | (2006.01) |
| A61K 31/167 | (2006.01) |
| A61K 31/4439 | (2006.01) |
| A61K 31/216 | (2006.01) |
| A61K 31/00 | (2006.01) |
| A61K 9/20 | (2006.01) |
| A61K 9/28 | (2006.01) |
| A61K 9/16 | (2006.01) |
| A61K 9/24 | (2006.01) |
| A61K 9/50 | (2006.01) |

(52) U.S. Cl.
CPC ............. *A61K 9/2846* (2013.01); *A61K 9/4808* (2013.01); *A61K 31/167* (2013.01); *A61K 31/4439* (2013.01); *A61K 31/216* (2013.01); *A61K 31/00* (2013.01); *A61K 9/2081* (2013.01); *A61K 9/2866* (2013.01); *A61K 9/1635* (2013.01); *A61K 9/209* (2013.01); *A61K 9/5026* (2013.01); *A61K 9/2886* (2013.01)
USPC ........... 424/744; 424/489; 514/338; 514/533; 514/629

(58) Field of Classification Search
CPC ....... A61K 2300/00; A61K 9/20; A61K 9/28; A61K 9/2086
USPC ................... 424/744, 489; 514/338, 533, 629
See application file for complete search history.

(56) References Cited

U.S. PATENT DOCUMENTS 6,544,556 B1    4/2003    Chen et al.
6,710,086 B1    3/2004    Lai et al.

OTHER PUBLICATIONS

Hyllested et al., British Journal of Anaesthesia, 2002, 88(2), 199-214.*
Ward et al., Clinical Rheumatology, 1995, 14(6), 656-662.*

* cited by examiner

*Primary Examiner* — Abigail Fisher
(74) *Attorney, Agent, or Firm* — Bio Intellectual Property Services LLC (Bio IPS);; O. (Sam) Zaghmout

(57) ABSTRACT

The present invention relates to pharmaceutical compositions in the form of fixed combination comprising non-steroidal anti-inflammatory drug or its single enantiomers or salts thereof, antipyretic-analgesic drug and proton pump inhibitor or its single enantiomers or salts thereof. The invention also relates to processes for the preparation of such compositions.

21 Claims, No Drawings

PHARMACEUTICAL COMPOSITIONS COMPRISING NON-STEROIDAL ANTIINFLAMMATORY DRUG, ANTIPYRETIC-ANALGESIC DRUG AND PROTON PUMP INHIBITOR

FIELD OF THE INVENTION

The present invention relates to pharmaceutical compositions in the form of fixed combination comprising non-steroidal anti-inflammatory drug or its single enantiomers or salts thereof, antipyretic-analgesic drug and proton pump inhibitor or its single enantiomers or salts thereof. The invention also relates to processes for the preparation of such compositions.

BACKGROUND OF THE INVENTION

Nonsteroidal anti-inflammatory drugs (hereinafter referred as "NSAIDs") are among the most commonly prescribed drugs. The ability of NSAIDs to treat inflammatory disorders is attributed to their ability to inhibit cyclooxygenase, the enzyme responsible for biosyntheses of the prostaglandins and certain autocoid inhibitors, including inhibitors of lipoxygenase and cyclooxygenase (such as cyclooxygenase-I and cyclooxygenase-II). Aceclofenac belongs to a group of NSAIDs. Chemically, aceclofenac is 2-[(2,6-dichlorophenyl)amino]benzeneacetic acid, carboxymethyl ester of formula I. It is used to relieve pain and inflammation in arthritic conditions. It is also indicated for the treatment of a form of arthritis called as ankylosing spondylitis, inflammatory disease of the joints and osteoarthritis.

FORMULA I

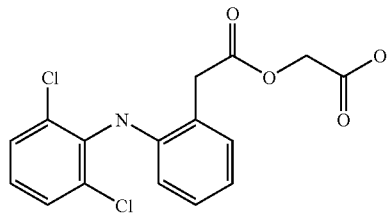

Proton pump inhibitors (PPIs) are a class of acid-labile pharmaceutical compounds that block gastric acid secretion pathways. They suppress gastric acid secretion by the inhibition of the $H^+$-$K^+$-ATPase enzyme system at the secretory surface of the gastric parietal cell. Rabeprazole sodium is one such proton pump inhibitor. Rabeprazole sodium, a substituted benzimidazole inhibits gastric acid secretion. Chemically, rabeprazole is 2-[[[4-(3-methoxypropoxy)-3-methyl-2-pyridinyl]-methyl]sulfinyl]-1H-benzimidazole sodium salt of formula II. It is indicated for the treatment of Symptomatic Gastroesophageal Reflux Disease (GERD), pathological hypersecretory conditions, including Zollinger-Ellison Syndrome and maintenance of healing of erosive or ulcerative Gastroesophageal Reflux Disease (GERD).

FORMULA II

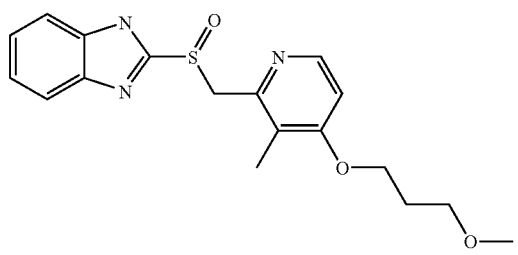

Paracetamol, also known as acetaminophen, 4'-hydroxyacetanilide, is a non-opiate, non-salicylate analgesic and antipyretic. Chemically, it is N-(4-hydroxyphenyl)ethanamide of Formula II. Acetaminophen provides temporary relief of minor aches and pains with heartburn or acid indigestion and upset stomach associated with these symptoms.

FORMULA III

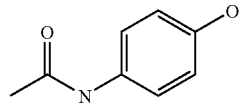

U.S. Pat. No. 6,544,556 discloses solid oral dosage forms comprising a diclofenac extended release tablet and an enterically coated proton-pump inhibitor without a separating layer between the proton pump inhibitor and, the enteric coat; these proton pump inhibitor enteric coated beads and the diclofenac tablet are contained within a capsule.

U.S. Pat. No. 6,926,907 discloses pharmaceutical compositions in unit dose form for oral administration comprising an acid inhibitor present in an amount effective to raise the gastric pH to at least 3.5 upon the administration of one or more of said unit dosage forms; and a non-steroidal anti-inflammatory drug (NSAID) in an amount effective to reduce or eliminate pain or inflammation upon administration of one or more of said unit dosage forms.

U.S. Pat. No. 6,869,615 discloses solid oral dosage forms comprising a population of substrates comprising a proton-pump inhibitor; an enteric coating layer coated over said substrates; and an NSAID coating layer coated over said enteric-coated substrates.

U.S. Patent Application No. 20050249806 discloses pharmaceutical compositions comprising a therapeutically effective amount of at least one acid labile proton pump inhibitor; at least one buffering agent in an amount sufficient to increase gastric fluid pH to a pH that prevents acid degradation of at least some of the proton pump inhibitor in the gastric fluid; and a therapeutically effective amount of at least one nonsteroidal anti-inflammatory drug.

U.S. Patent Application No. 20050163847 discloses solid oral dosage forms comprising a first portion comprising a therapeutically effective amount of an NSAID; and a coating comprising a therapeutically effective amount of an anti ulcerative compound; said coating at least partially surrounding said first NSAID portion.

However, despite the therapeutic benefits of NSAIDs, their use is often limited by an increased risk of gastrointestinal side effects, in particular upper gastrointestinal side effects such as peptic ulceration and dyspeptic symptoms. It is also well known that NSAIDs have the potential to cause gastrointestinal (GI) bleeding through a variety of mechanisms related to their topical and systemic effects. The GI bleeding may depend on the length of the treatment and on the particular drug. This problem is important in cases where the therapy must be continued for a long period of time.

Therefore, there exists a need in the art for a combination formulation, which includes an NSAID, analgesic-antipyretic with proton pump inhibitor to reduce the occurrence of gastro-intestinal side effects associated with NSAID treatment.

SUMMARY OF THE INVENTION

In one general aspect there is provided a solid dosage form for oral administration comprising:
 a) an inner core comprising a therapeutically effective amount of a proton pump inhibitor, an inert intermediate layer surrounding the core and an enteric coating over the intermediate layer; and b) outer core comprising granules of antipyretic-analgesic and antiarthritic-antiinflammatory agents in therapeutically effective amounts.

Embodiments of the solid dosage form may include one or more of the following features. For example, the solid dosage form may further include one or more pharmaceutically acceptable excipients that include diluents, fillers, binders, lubricants, sweeteners, coloring and flavoring agents, glidants, and the like.

The term 'proton pump inhibitors' as used herein includes, but not limited to, omeprazole, lansoprazole, rabeprazole, pantoprazole and leminoprazole, including isomers, enantiomers, tautomers and alkaline salts thereof.

The term 'non-steroidal anti-inflammatory' drugs as used herein includes, but not limited to, the group consisting of aceclofenac, salicylates, indomethacin, flurbiprofen, diclofenac, ketorolac, naproxen, piroxicam, tebufelone, ibuprofen, etodolac, nabumetone, aminopyrine, phenylbutazone, oxyphenbutazone, fenoprofen, flufenamic acid, ketoprofen, mefenamic acid, phenacetin, sulindac, including isomers, enantiomers, tautomers and alkaline salts thereof.

The term 'analgesic-antipyretic agents' as used herein includes, but not limited to, acetaminophen, aspirin, ibuprofen, and the like.

The intermediate layer also can be called as a seal coat and may be formed from an inert film forming polymers. The intermediate layer may be surrounded by an outer enteric coat.

In another general aspect there is provided a solid dosage form for oral administration comprising:
a) an enteric coated tablet comprising a core containing a therapeutically effective amount of rabeprazole sodium, an inert intermediate layer surrounding the core and an enteric coating over the intermediate layer; and
b) granules comprising therapeutically effective amounts of aceclofenac and paracetamol,
wherein the enteric-coated tablet and the granules are contained within a hard gelatin capsule.

Embodiments of the solid dosage form may include one or more of the following features. For example, the solid dosage form may further include one or more pharmaceutically acceptable excipients that include diluents, fillers, binders, lubricants, sweeteners, coloring and flavoring agents, glidants, and the like.

In another general aspect there is provided a solid dosage form for oral administration comprising:
a) enteric coated pellets comprising a core containing a therapeutically effective amount of rabeprazole sodium, an inert intermediate layer surrounding the core and an enteric coating over the intermediate layer; and
b) granules comprising therapeutically effective amounts of aceclofenac and paracetamol,
wherein the enteric-coated pellets and the granules are contained within a hard gelatin capsule.

Embodiments of the solid dosage form may include one or more of the following features. For example, the solid dosage form may further include one or more pharmaceutically acceptable excipients that include diluents, fillers, binders, lubricants, sweeteners, coloring and flavoring agents, glidants, and the like.

In another general aspect there is provided a tablet in tablet dosage form for oral administration comprising:
a) an inner tablet comprising a core comprising a therapeutically effective amount of rabeprazole sodium, an inert intermediate layer surrounding the core and an enteric coating over the inert intermediate layer; and
b) outer core comprising granules comprising therapeutically effective amounts of aceclofenac and paracetamol.

Embodiments of the dosage form may include one or more of the following features. For example, the dosage form may further include one or more pharmaceutically acceptable excipients that include diluents, fillers, binders, lubricants, sweeteners, coloring and flavoring agents, glidants, and the like.

In another general aspect there is provided a solid dosage form for oral administration comprising:
a) enteric coated pellets comprising a core containing a therapeutically effective amount of rabeprazole sodium, an inert intermediate layer surrounding the core and an enteric coating over the intermediate layer; and
b) granules comprising therapeutically effective amounts of aceclofenac and paracetamol,
wherein the enteric-coated pellets and the granules are further compressed into bilayer tablets.

Embodiments of the solid dosage form may include one or more of the following features. For example, the solid dosage form may further include one or more pharmaceutically acceptable excipients that include diluents, fillers, binders, lubricants, sweeteners, coloring and flavoring agents, glidants, and the like.

In another general aspect there is provided a pharmaceutical composition comprising a triple combination of rabeprazole sodium, aceclofenac and paracetamol, wherein the rabeprazole has a dissolution profile in USP type II Apparatus in 6.8-pH phosphate buffer as a dissolution medium at 37° C.±2° C.:
at least 50% w/w of rabeprazole is released within first 5 minutes, or
at least 60% of rabeprazole is released within first 10 minutes, or
at least 70% of rabeprazole is released within 15 minutes, or
at least 80% of rabeprazole is released within 30 minutes or
at least 90% of rabeprazole is released within 45 minutes, and wherein the release of rabeprazole from the composition is independent of the release of aceclofenac and paracetamol.

Embodiments of the solid dosage form may include one or more of the following features. For example, the dissolution test may be carried out using USP type II apparatus. For determining the release rate of enteric coated rabeprazole 0.1N HCl may be used as a dissolution medium for first two hours and further dissolution test may be carried out with 6.8-pH phosphate buffer replacing 0.1 N HCl at 37° C.±2° C.

In another general aspect there is provided a pharmaceutical composition comprising a triple combination of rabeprazole sodium, aceclofenac and paracetamol, wherein the aceclofenac has a dissolution profile in USP type II Apparatus in 6.8-pH phosphate buffer as a dissolution medium at 37° C.±2° C.:
at least 50% w/w of aceclofenac is released within first 5 minutes, or
at least 70% of aceclofenac is released within first 10 minutes, or
at least 80% of aceclofenac is released within first 15 minutes, or
at least 85% of aceclofenac is released within first 30 minutes or
at least 95% of aceclofenac is released within first 45 minutes,
and wherein the release of aceclofenac from the composition is independent of the release of rabeprazole and paracetamol.

In another general aspect there is provided a pharmaceutical composition comprising a triple combination of rabeprazole sodium, aceclofenac and paracetamol, wherein the paracetamol has a dissolution profile in USP type II Apparatus in 6.8-pH phosphate buffer as a dissolution medium at 37° C.±2° C.:

- at least 50% w/w of paracetamol is released within first 5 minutes, or
- at least 60% of paracetamol is released within first 10 minutes, or
- at least 70% of paracetamol is released within first 15 minutes, or
- at least 80% of paracetamol is released within first 30 minutes or
- at least 90% of paracetamol is released within first 45 minutes, and wherein the release of paracetamol from the composition is independent of the release of rabeprazole and aceclofenac.

The details of one or more embodiments of the inventions are set forth in the description below. Other features, objects and advantages of the inventions will be apparent from the description and claims.

DETAILED DESCRIPTION OF THE INVENTION

The present invention is directed to pharmaceutical compositions that include a triple combination of at least one non-steroidal anti-inflammatory drug or one of its single enantiomers or salts thereof, one antipyretic-analgesic drug, one proton pump inhibitor or one of its single enantiomers or salts thereof, in a single oral pharmaceutical dosage form. These compositions reduce gastric side effects of long term administered antipyretic-analgesic and antiarthritic-antiinflammatory drugs and enhances the patient's compliance.

Proton pump inhibitors are potent inhibitors of gastric acid secretion, inhibiting $H^+$-$K^+$-ATPase, the enzyme involved in the final step of hydrogen ion production in the parietal cells. The term proton pump inhibitors as used herein, include but not limited to rabeprazole, omeprazole, lansoprazole, pantoprazole and leminoprazole, including isomers, enantiomers and tautomers thereof, and alkaline salts thereof.

Non-steroidal anti-inflammatory drugs are used to treat inflammatory conditions. The term non-steroidal anti-inflammatory drugs as used herein, includes but not limited to, the group consisting of salicylates, indomethacin, flurbiprofen, diclofenac, ketorolac, naproxen, piroxicam, tebufelone, ibuprofen, etodolac, nabumetone, aceclofenac, aminopyrine, phenylbutazone, oxyphenbutazone, fenoprofen, flufenamic acid, ketoprofen, mefenamic acid, phenacetin, sulindac, including isomers, enantiomers and tautomers thereof, and alkaline salts thereof.

Analgesic-antipyretic agents are the drugs that are used to alleviate pain and to reduce fever. The term Analgesic-antipyretic agents as used herein, includes but not limited to, aspirin, acetaminophen, ibuprofen, and the like.

These active agents or drugs, the enantiomers thereof or their mixtures, and the pharmaceutically acceptable acid addition salts thereof may be formulated into ordinary dosage forms such as, for example, tablets, capsules, pills, solutions, etc. and in these cases, the medicaments can be prepared by conventional methods, including a therapeutically effective amounts of the active agents, or their pharmaceutically acceptable salts, along with a pharmaceutically acceptable carrier, and optionally but desirably, pharmaceutically acceptable excipients.

By "therapeutically effective amount" is meant the quantity of a compound or composition according to the invention necessary to prevent, cure or at least partially arrest the symptoms of the disorder and its complications. Amounts effective to achieve this goal will, of course, depend on the severity of the disease and the weight and general state of the patient. Typically, dosages used in vitro may provide useful guidance in the amounts useful for in situ administration of the pharmaceutical composition, and animal models may be used to determine effective dosages for treatment of particular disorders. Various considerations are described, for example, in Gilman et al., eds., 1900, "Goodman and Gilman's: The Pharmaceutical Bases of Therapeutics," 8th ed., Pergamon Press; and Remington's Pharmaceutical Sciences," 1990, 17th ed., Mack Publishing Co., Easton, Pa., each of which is hereby incorporated by reference.

The pharmaceutical compositions containing the proton pump inhibitors; NSAIDs and analgesics-antipyretics disclosed herein are administered orally. The combination can be employed in admixture with pharmaceutically acceptable excipients. The pharmaceutically acceptable excipients can be diluents, fillers, binders, lubricants, sweeteners, coloring and flavoring agents, glidants, and the like. The binders may be one or more of starch, sugars, gums, low molecular weight hydroxypropylmethyl cellulose, polyvinyl pyrrolidone and hydroxypropyl cellulose and the like. The lubricants may be one or more talc, magnesium stearate, polyethylene glycol, hydrogenated vegetable oils, stearic acid, sodium stearyl fumarate and sodium benzoate and the like. The glidants may be one or both of colloidal silicon dioxide and talc or magnesium stearate, and the like. Suitable coloring and flavoring agents include those approved for use by the United States Food and Drug Administration (FDA) and are well known to those skilled in the art.

The intermediate layer also can be called as a seal coat and may be formed from inert film forming polymers. The film forming polymers comprise one or more of suitable cellulose ethers. Suitable cellulose ethers may include hydroxypropyl methylcellulose, hydroxypropyl cellulose and mixtures thereof. The film former may be applied as a solution.

The intermediate layer is surrounded by outer enteric coat. The enteric coating may include pharmaceutically acceptable enteric coating forming polymers, such as methacrylic acid/methyl methacrylate copolymers such as, Eudragit L or cellulose derivatives such as, carboxymethyl cellulose, cellulose acetate phthalate, hydroxypropylmethyl cellulose phthalate, and other suitable polymers.

The inner core may be prepared by direct compression, dry granulation or wet granulation. The core containing proton pump inhibitor may be present in the form of enteric-coated core with or without intermediate layer surrounding the core.

The dosage form may be in the form of a tablet, capsule, pellet, granule, tablet in a tablet, tablet in a capsule or a layered tablet.

The tablet in tablet dosage form may be prepared by first compressing the enteric coated proton-pump inhibitor drug followed by compressing granules containing NSAIDs and analgesics-antipyretics.

The layered tablet may be prepared by forming first layer of enteric-coated granules followed by layers containing NSAIDs and analgesic-antipyretics.

The capsules may be prepared by filling in the empty capsule shells enteric-coated proton-pump inhibitor drug containing pellet/tablet along with granules containing NSAIDs and analgesics-antipyretics.

The enteric-coated tablets may be prepared by direct compression, dry granulation or by wet granulation. Rabeprazole sodium, Pearlitol SD 200, light Magnesium oxide, sodium carbonate (anhydrous), L-Hydroxy propyl cellulose (LH-11), crospovidone INF and other ingredients were sifted through mesh, mixed well and compressed into tablets. The core tablets of rabeprazole were coated with coating solution. These coated tablets were then enteric coated with organic dispersion of methacrylic acid copolymer.

The enteric-coated pellets may be prepared by mixing rabeprazole sodium, colloidal silicon dioxide, and magnesium oxide along with other suitable ingredients, mixed well and compressed to get desired size pellets. These pellets were further coated with coating solution and then enteric coated with organic dispersion of methacrylic acid copolymer.

The granules of aceclofenac and paracetamol may be prepared by dry granulation or by wet granulation. Aceclofenac, paracetamol and pre-gelatinized starches were mixed and granulated with suitable binder. These granules were further lubricated.

The dissolution test may be carried out using USP type II apparatus. For determining the release rate of enteric coated rabeprazole 0.1N HCl may be used as dissolution medium for first two hours and further dissolution test is carried out with 6.8-pH phosphate buffer replacing 0.1 N HCl at 37° C.±2° C.

The dissolution test of aceclofenac and paracetamol may be carried out using USP type II apparatus and 6.8-pH phosphate buffer as dissolution medium at 37° C.±2° C. The release rate of aceclofenac is independent of the release of paracetamol.

The present invention is further illustrated by the following examples which are provided merely to be exemplary of the invention and do not limit the scope of the invention. Certain modifications and equivalents will be apparent to those skilled in the art and are intended to be included within the scope of the present invention.

Example 1

The composition of batches is provided in table 1. Following formulations are representatives of the preferred compositions of the present invention. The preparation of example 1 is detailed below. The present example is directed to a triple combination of proton pump inhibitor (e.g. rabeprazole sodium), NSAID (e.g. aceclofenac) and analgesic-antipyretic (e.g. paracetamol).

Table 1 provides composition of batches of the present invention.

| INGREDIENTS | Example (mg/tab) |
|---|---|
| INNER TABLET | |
| Rabeprazole sodium | 100.0 |
| Pearlitol SD 200 | 39.0 |
| Light Magnesium oxide | 2.5 |
| Sodium carbonate | 2.0 |
| L-Hydroxy propyl cellulose | 3.0 |
| Glyceryl behenate | 0.5 |
| Crospovidone INF | 105.0 |
| Sodium metabisulphite | 1.0 |
| | 252.0 |
| SEAL COAT | |
| Organic dispersion of Hydroxy propyl cellulose | Till weight gain reaches to 2.5% |
| ENTERIC COAT | |
| Methacrylic acid copolymer | Till weight gain reaches to 10.0% |
| Talc | |
| Dimethyl phthalate | |
| Titanium dioxide | |
| Iron oxide red | |

| INGREDIENTS | Example (mg/tab) |
|---|---|
| GRANULES | |
| Aceclofenac | 100.0 |
| Paracetamol | 500.0 |
| Pre-gelatinized starch | 20.0 |
| Povidone (PVPK-30) | 20.0 |
| Maize Starch | 20.0 |
| Sodium starch glycolate | 20.0 |
| Microcrystalline cellulose | 255.0 |
| Talc | 10.0 |
| Magnesium stearate | 5.0 |
| Total | 950.0 |

Process for the Manufacture of Enteric Coated Rabeprazole Tablet—

All the above ingredients listed for inner tablet were sifted through ASTM mesh, mixed well and compressed into tablets. The core tablets of rabeprazole were seal coated with organic dispersion of hydroxy propyl cellulose. The seal coated tablets were then enteric coated with organic dispersion of methacrylic acid copolymer, talc, dimethyl phthalate, titanium dioxide and iron oxide red.

Procedure for Preparation of Enteric-Coated Rabeprazole Sodium Pellets—

The bend of rabeprazole sodium, light magnesium oxide, colloidal silicon dioxide was prepared, sifted through sieve and mixed well to give uniform drug blend. Povidone was dissolved in isopropyl alcohol to give clear binder solution; this binder solution was sprayed on the blend until blend gets sufficient moisture, pellets were prepared and dried. The pellets of rabeprazole sodium were seal coated with solution of hydroxypropylmethyl cellulose, magnesium carbonate and triethyl citrate in isopropyl alcohol and methylene chloride. The seal coated pellets then enteric coated with aqueous dispersion of Eudragit L30D 55, sodium hydroxide, triethyl citrate, talc and titanium dioxide and dried.

Process for the Manufacture of Aceclofenac and Paracetamol Granules—

Aceclofenac, paracetamol, pre-gelatinized starch were mixed and granulated with povidone-starch paste. Wet granules were passed through sieve and dried in fluidized bed dryer. The dried granules were passed through sieve and mixed with sodium starch glycolate, microcrystalline cellulose, and talc and magnesium stearate.

These tablets/pellets were filled in hard gelatin capsules along with aceclofenac and paracetamol granules.

The enteric-coated rabeprazole tablets along with aceclofenac-paracetamol lubricated granules were compressed using tablet in tablet machine.

The bilayer tablet was compressed in which inner layer was made up of rabeprazole sodium. This bilayer tablet was further coated with organic dispersion of hydroxypropylmethyl cellulose.

Table 2 and 3 provides the dissolution data for the triple combination dosage form prepared as per the Formula given in Table 1.

For determination of drug release rate of aceclofenac and paracetamol, USP Type 2 Apparatus was used wherein 6.8 pH phosphate buffer was used as a dissolution medium and for determination of drug release rate of rabeprazole, USP Type 2 Apparatus was used wherein 0.1N hydrochloric acid was used as a medium (2 hrs), followed by 1000 ml of 6.8 pH phosphate buffer (1 hr).

TABLE 2

Dissolution data of aceclofenac-paracetamol as per the present invention

| Time (minutes) | % Released of aceclofenac | % Released of paracetamol |
| --- | --- | --- |
| 0 | 0 | 0 |
| 5 | 63.72 | 62.19 |
| 10 | 78.90 | 72.58 |
| 15 | 88.32 | 81.46 |
| 30 | 91.13 | 90.33 |
| 45 | 98.72 | 97.29 |

TABLE 3

Dissolution data of rabeprazole as per the present invention

| Time (minutes) | % Released of rabeprazole |
| --- | --- |
| 0.1 N HCl | |
| 120 | 0.0 |
| 6.8 pH phosphate buffer | |
| 0 | 0.00 |
| 5 | 63.02 |
| 10 | 73.57 |
| 15 | 81.64 |
| 30 | 89.42 |
| 45 | 95.38 |

While the present invention has been described in terms of its specific embodiments, certain modifications and equivalents will be apparent to those skilled in the art and are intended to be included within the scope of the present invention.

We claim:

1. A tablet dosage form for oral administration comprising: a) an inner core consisting of a therapeutically effective amount of a proton pump inhibitor, an inert intermediate layer surrounding the core and an enteric coating over the intermediate layer; and b) an outer layer comprising granules of paracetamol and one or more antiarthritic-antiinflammatory agents in therapeutically effective amounts, wherein the dosages form results in reduced gastric effects on administration.

2. The tablet dosage form according to claim 1, wherein the proton pump inhibitor is selected from the group consisting of rabeprazole, omeprazole, lansoprazole, pantoprazole and leminoprazole, including isomers, enantiomers and tautomers thereof, and alkaline salts thereof.

3. The tablet form according to claim 1, wherein the antiarthritic-antiinflammatory agent is selected from the group consisting of aceclofenac, salicylates, indomethacin, flurbiprofen, diclofenac, ketorolac, naproxen, piroxicam, tebufelone, ibuprofen, etodolac, nabumetone, aminopyrine, phenylbutazone, oxyphenbutazone, fenoprofen, flufenamic acid, ketoprofen, mefenamic acid, phenacetin, sulindac, including isomers, enantiomers and tautomers thereof, and alkaline salts thereof.

4. The tablet dosage form according to claim 1, wherein the proton pump inhibitor is present in an amount effective to inhibit gastrointestinal side effects associated with NSAIDs.

5. The tablet dosage form according to claim 1, wherein the intermediate layer comprises one or more of film forming polymers.

6. The tablet dosage form according to claim 5, wherein the film forming polymers comprise one or more of hydroxypropyl methylcellulose, hydroxypropyl cellulose and mixtures thereof.

7. The tablet dosage form according to claim 1, wherein the enteric coating comprises one or more of enteric coating forming polymers.

8. The tablet dosage form according to claim 7, wherein the enteric coating forming polymers comprise one or more of methacrylic acid/methyl methacrylate copolymers, carboxymethyl cellulose, cellulose acetate phthalate, hydroxypropyl methylcellulose phthalate and mixtures thereof.

9. The tablet dosage form according to claim 1, further comprising one or more pharmaceutically acceptable excipients.

10. The tablet dosage form according to claim 9, wherein the pharmaceutically acceptable excipients comprise one or more of diluents, fillers, binders, lubricants, sweeteners, coloring and flavoring agents, and glidants.

11. A solid dosage form for oral administration comprising: a) an enteric coated tablet comprising a core consisting of a therapeutically effective amount of rabeprazole sodium, an inert intermediate layer surrounding the core and an enteric coating over the intermediate layer; and b) granules comprising therapeutically effective amounts of aceclofenac and paracetamol, wherein the enteric-coated tablet and the granules are contained within a hard gelatin capsule, wherein the dosage form results in reduced gastric effects on administration.

12. A solid dosage form for oral administration comprising: a) enteric coated pellets comprising a core consisting of a therapeutically effective amount of rabeprazole sodium, an inert intermediate layer surrounding the core and an enteric coating over the intermediate layer; and b) granules comprising therapeutically effective amounts of aceclofenac and paracetamol, wherein the enteric-coated pellets and the granules are contained within a hard gelatin capsule, wherein the dosages form results in reduced gastric effects on administration.

13. A solid dosage form according to claim 12, wherein the enteric-coated tablet is prepared by direct compression, dry granulation or wet granulation.

14. A tablet dosage form for oral administration comprising: a) an inner tablet comprising a core consisting of a therapeutically effective amount of rabeprazole sodium, an inert intermediate layer surrounding the core and an enteric coating over the inert intermediate layer; and b) an outer layer comprising granules comprising therapeutically effective amounts of aceclofenac and paracetamol, wherein the dosage form results in reduced gastric effects on administration.

15. A solid dosage form for oral administration comprising: a) enteric coated pellets comprising a core consisting of a therapeutically effective amount of rabeprazole sodium, an inert intermediate layer surrounding the core and an enteric coating over the intermediate layer; and b) granules comprising therapeutically effective amounts of aceclofenac and paracetamol, wherein the enteric-coated pellets and the granules are further compressed into bilayer tablets, wherein the dosages form results in reduced gastric effects on administration.

16. The tablet dosage form according to claim 15, wherein the rabeprazole is present in a therapeutically effective amount to reduce the side effects associated with aceclofenac and paracetamol.

17. A tablet dosage form pharmaceutical composition comprising a triple combination of rabeprazole sodium, aceclofenac and paracetamol, wherein the rabeprazole has a dissolution profile in USP type II Apparatus in 6.8 pH phosphate buffer as a dissolution medium at 37° C.±2° C., at least 50% w/w of rabeprazole is released within first 5 minutes, or at least 60% of rabeprazole is released within first 10 minutes, or at least 70% of rabeprazole is released within 15 minutes, or at least 80% of rabeprazole is released within 30 minutes or at least 90% of rabeprazole is released within 45 minutes, and wherein the release of rabeprazole from the composition is independent of the release of aceclofenac and paracetamol, wherein the dosage form results in reduced gastric effects on administration wherein said dosage form comprises an inner core consisting of rabeprazole sodium.

18. The pharmaceutical composition according to claim 17, wherein the rabeprazole sodium is in enteric coated form.

19. The pharmaceutical composition according to claim 17, wherein the release of enteric coated rabeprazole sodium is less than 5% when measured using USP type II apparatus in 0.1N HCl for first two hours.

20. A tablet dosage form pharmaceutical composition comprising a triple combination of rabeprazole sodium, aceclofenac and paracetamol, wherein the aceclofenac has a dissolution profile in USP type II Apparatus in 6.8 pH phosphate buffer as a dissolution medium at 37° C.±2° C., at least 50% w/w of aceclofenac is released within first 5 minutes, or at least 70% of aceclofenac is released within first 10 minutes, or at least 80% of aceclofenac is released within first 15 minutes, or at least 85% of aceclofenac is released within first 30 minutes or at least 95% of aceclofenac is released within first 45 minutes, and wherein the release of aceclofenac from the composition is independent of the release of rabeprazole and paracetamol, wherein the dosage form results in reduced gastric effects on administration wherein said dosage form comprises an inner core consisting of rabeprazole sodium.

21. A tablet dosage form pharmaceutical composition comprising a triple combination of rabeprazole sodium, aceclofenac and paracetamol, wherein the paracetamol has a dissolution profile in USP type II Apparatus in 6.8 pH phosphate buffer as a dissolution medium at 37° C.+2° C., at least 50% w/w of paracetamol is released within first 5 minutes, or at least 60% of paracetamol is released within first 10 minutes, or at least 70% of paracetamol is released within first 15 minutes, or at least 80% of paracetamol is released within first 30 minutes or at least 90% of paracetamol is released within first 45 minutes, and wherein the release of paracetamol from the composition is independent of the release of rabeprazole and aceclofenac, wherein the dosages form results in reduced gastric effects on administration wherein said dosage form comprises an inner core consisting of rabeprazole sodium.

* * * * *